United States Patent [19]

Grass

[11] 4,053,782

[45] Oct. 11, 1977

[54] DEVICE FOR ALIGNING AN X-RAY SOURCE WITH AN IMAGE RECEPTOR

[75] Inventor: Joseph J. Grass, Brookfield, Wis.

[73] Assignee: General Electric Company, Schenectady, N.Y.

[21] Appl. No.: 721,555

[22] Filed: Sept. 8, 1976

[51] Int. Cl.$^2$ ............................................. G03B 41/16
[52] U.S. Cl. .................................. 250/491; 250/320; 250/476
[58] Field of Search ............... 250/491, 476, 312, 320, 250/321, 322, 323

[56] References Cited

U.S. PATENT DOCUMENTS

| | | | |
|---|---|---|---|
| 1,917,433 | 7/1933 | Cressler | 250/476 |
| 3,577,160 | 5/1971 | White | 250/476 |

*Primary Examiner*—Craig E. Church
*Attorney, Agent, or Firm*—Ralph G. Hohenfeldt

[57] ABSTRACT

A device for aligning the central ray of an x-ray beam with the center of an image receptor comprises a metal tube in a mounting which is provided with means for establishing the axis of the tube perpendicular to the plane of the image receptor or other plane which is perpendicular to the central ray. The tube is mounted in such manner that the region around it is x-ray permeable. The mounting is adapted for being moved in parallelism with the plane such that alignment of the central ray with a point on the receptor may be determined when the circular shadow cast by the outside of the tube is concentric with the circular image of the tube bore.

8 Claims, 6 Drawing Figures

U.S. Patent  Oct. 11, 1977  4,053,782
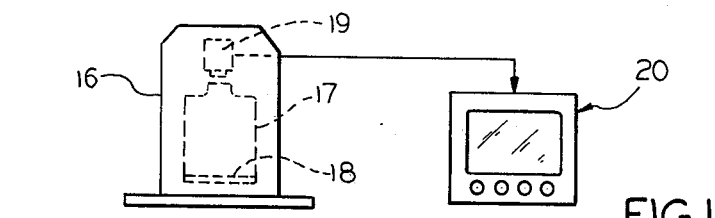
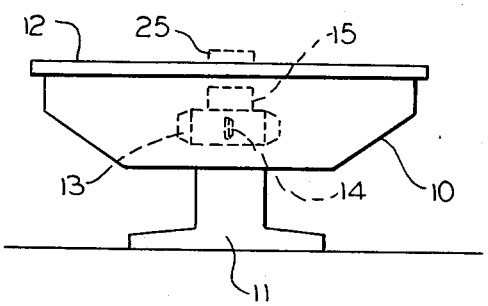
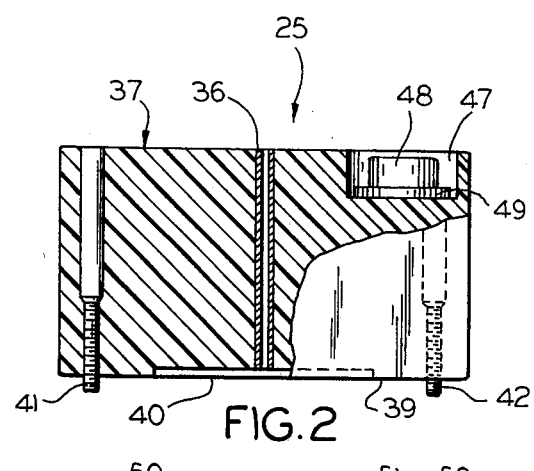
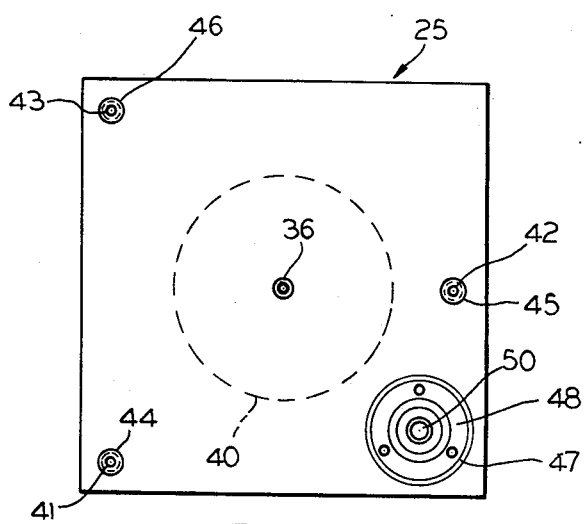
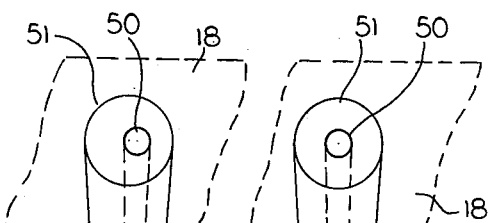
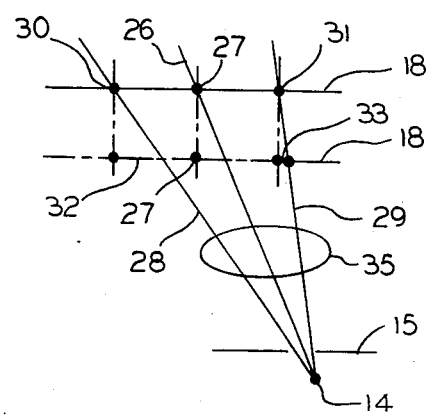
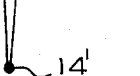

DEVICE FOR ALIGNING AN X-RAY SOURCE WITH AN IMAGE RECEPTOR

BACKGROUND OF THW INVENTION

This invention pertains to a beam alignment device for use with diagnostic x-ray apparatus.

In one type of diagnostic x-ray apparatus the x-ray tube is mounted inside of the body of the patient's supporting x-ray table. An image receptor such as an image intensifier or a radiographic film is mounted above the table top in such manner that the image receptor may be moved toward and away from the x-ray tube. In this arrangement, it is necessary to have the central ray of the beam, which diverges from the focal spot of the tube, perpendicular to and centered on the plane of the image receptor. As is well known, if the central ray is not perpendicular and centered, the central ray will shift laterally along the receptor plane as the plane is raised and lowered relative to the focal spot. A consequence is that the edges of the collimated x-ray beam will not coincide with the edges of the receptor plane at all levels. Thus, the beam may fall short of the edge of the receptor plane on one side and overlap on the other side, which in the latter case, results in part of the x-ray image being cut off and not recorded. This is undesirable, not only because of the loss of information in the image, but also the patient is exposed to radiation dosage which produces no information.

SUMMARY OF THE INVENTION

An object of the present invention is to provide a device for aligning an x-ray source with an image receptor such that the aforementioned problems resulting from misalignment may be overcome.

Other objects are to provide an aligning device which is rugged, inexpensive and easy to use.

In general terms, the aligning device comprises a metal tube in a mounting which allows the x-ray beam to pass generally coaxially along the inside and the outside of the tube. When the metal tube is positioned perpendicular to the x-ray tube horizontal reference plane and in vertical alignment with the tube focal spot, the projected image of the tube outside diameter and inside diameter are concentric. If the metal tube bore is not aligned precisely with the central ray of the beam emanating from the focal spot, the outside diameter and inside diameter images which are projected on the receptor plane will not be concentric. The device is then moved until concentricity is obtained on the receptor plane and then the plane is shifted as required until the concentric image coincides with the center of the plane. The center of the receptor plane will then be on the vertical line of the focal spot regardless of the elevation to which the receptor plane is set.

A more detailed description of the construction and use of the new alignment device will now be set forth in reference to the drawing.

DESCRIPTION OF THE DRAWING

FIG. 1 is a diagram of one type of diagnostic x-ray system in which the new aligning device may be employed;

FIG. 2 is a side elevation view of the device, partly in section;

FIG. 3 is a plan view of the device;

FIG. 4 is a diagram for facilitating discussion of the problems of misalignment; and FIGS. 5 and 6 are diagrams for illustrating the nature of the images on the receptor plane when there is misalignment and alignment, respectively.

DESCRIPTION OF A PREFERRED EMBODIMENT

A typical x-ray diagnostic system wherein the new device may be used to align the central ray or ray bundle of an x-ray beam with the image receptor center is shown diagrammatically in FIG. 1. The system comprises an x-ray table having an enclosed metal body 10 supported on a stand 11. Usually the body 10 is tiltable on stand 11 about a laterally extending axis which, in this case, means about an axis that is perpendicular to the plane of the drawing. The table has a patient supporting top 12. An x-ray tube casing 13 is mounted in any well-known manner within body 10. The details of the x-ray tube within the casing are not shown but it will be understood that the tube has the usual target 14 on which an electron beam impinges to produce a focal spot from which an x-ray beam emanates. An x-ray beam collimator 15 is coupled with the x-ray casing and performs it usual function of defining the boundaries of the diverging x-ray beam which is projected through the table top 13 and a patient reposed thereon.

Mounted above the table top 12, in this example, is a casing 16 which, except for its bottom, is x-ray impervious. Inside of the casing there is a conventional x-ray image-to-optical-image converter tube, commonly known as an x-ray tube 17 which is shown in dashed lines. The x-ray image impinges on a receptor plane 18 and it is converted to an optical image within tube 17 which image may be viewed with a television camera 19 and displayed on a television montior 20. In this example, the image receptor 18 is the input fluorescent screen of image tube 17 but it should be understood that the image receptor can be a radiographic film or a direct viewing fluorscopic screen for other recording medium.

In FIG. 1, the new beam aligning device is generally designated by the reference numeral 25. It is shown positioned on table top 12 approximately as it would be during the aligning procedure but it will be understood that the device 25 is removed when central ray alignment has been accomplished. X-ray tube casings such as 13 are usually provided with a horizontal reference plane and with means for adjusting the position of the casing until the reference plane is parallel with the plane of table top 12 in which case the central ray of the x-ray beam emanating from target 14 will be perpendicular to the table top 12.

As indicated earlier, during diagnostic procedures, it is necessary to position the image intensifier tube 17 and its receptor plane 18 at various distances from the x-ray tube focal spot on target 14 and it is necessary for the center of the image receptor plane 18 to remain on the same vertical line as the focal spot if image distortion and displacement is to be avoided.

Geometrical considerations of alignment and misalignment will now be discussed in reference to FIG. 4 which shows an exaggerated case of misalignment for the sake of illustration. Assume that the image receptor plane 18, illustrated by a solid line, is at a particular elevation relative to focal spot 14' such that the central x-ray 26 or small central ray bundle is coincident with the center 27 of the receptor plane. The boundary rays 28 and 29 are so defined by collimator 15 that the edges 30 and 31 of the receptor field coincident with the boundary rays. In other words, there is edge-to-edge coincidence and center coincidence when the plane of the image receptor 18 is at the illustrated level. The image formed on the receptor will be that which is within the limits of boundary rays 28 and 29 as they pass through a body 35. In this diagram it will be obvious that the center 27 of the receptor is not on the same vertical line as focal spot 14. Now, it will be observed that if the receptor plane 18 is moved to its dashed line position closer to focal spot 14, the central x-ray 26 will no longer pass through center point 27 and there will be an edge area 32 on the receptor plane on which no image will be recorded. On the other edge, a portion 33 of the image will be cut off. If the receptor plane 18 is moved farther away from focal spot 14 it will be obvious that there will be a reversal between the cut off and unexposed edges.

The new device for aligning the center point 27 of the receptor 18 on the same vertical line as focal spot 14 will now be described in greater detail in reference to FIGS. 2 and 3. The device comprises a metal tube 36 which may be stainless steel or other metal which has high x-ray absorption. In a commercial embodiment, the tube is about 2 inches long and has as outside diameter of about 0.073 inch and a wall thickness of about 0.016 inch. Thus, the bore of the tube is about 0.041 inch. These dimensions are given for the purpose of illustration and should not be construed as limiting for the tube may be a little smaller or larger and longer but preferably, it should not be substantially shorter. The metal tube 36 should have a length which is much longer than its outside diameter.

Mounting means are provided for the tube 36 in the form of a plastic block 37 which, in a commercial embodiment, is methyl methacrylate such as a material identified by either of the trademarks "Lucite" or "Plexiglass". Any suitable material which is transparent to x-radiation may be used but transparency to light is not essential. The tube 36 may be mounted in other ways as long as passage of radiation coaxially therewith and without significant absorption is permitted.

Tube 36 is cemented in a machined hole in block 37 perpendicularly to the upper surface 38 of the block and to its preferably planar lower surface 39. The block has a circular recess 40 in its bottom. The block also has three leveling screws 41, 42 and 43 threaded into it. The tips of the screws 41–43 extend out from the bottom of the block. The screws are accessible through counterbored holes 44, 45 and 46 for being turned with a screwdriver or Allen wrench. By proper adjustment of the screws, the axis of tube 36 may be placed in precise perpendicularity with the x-ray table top 12 and coincident with the central x-ray beam when the device is set on the top.

Block 37 has a recess 47 in which there is a bubble level device 48 of a readily commercially available type. The bottom 49 of recess 47 is made parallel to the transverse top and bottom planes 38 and 39 so it is in true perpendicularity with the axis of tube 36. When the device is placed on the x-ray table top, leveling screws 41–43 are adjusted until the bubble 50 in the level is centered in which case the axis of tube 36 is truly perpendicular.

Use of the device to align a selected ray in a diverging ray beam is illustrated in FIGS. 5 and 6 where the tube 36 is shown diagrammatically but the plastic mounting block and leveling elements are omitted. Assume in reference to FIGS. 5 and 6 that the alignment procedure is in progress. The device 25 will be set over the x-ray tube as closely as possible to the central ray of the beam as illustrated in FIG. 1. The image receptor plane 18 will be in spaced relationship to the focal spot 14 and the location of tube 36 relative to the receptor plane and focal spot will be such, preferably, that the image of the tube appearing on the receptor will be magnified by at least a factor of two. The leveling screws 41–43 are then adjusted until the bubble in level 48 is centered at which time the axis of metal tube 36 will be perpendicular to the horizontal reference plane of the x-ray tube casing 13 and to the table top and the axis will be parallel with and possibly coincident with the central ray path. When the set up is made, the x-ray source is turned on and the image of the tube 36 will be cast on the receptor 18. In the FIG. 1 apparatus, the image on the receptor may be viewed on television monitor 20. If, as is the case in FIG. 5, the axis of the tube 36 is laterally displaced from the vertical central ray of the x-ray beam, the circular pattern 50 of the x-ray image resulting from the radiation passing through the bore of tube 36 will be eccentric with respect to the generally circular pattern of the shadow 51 cast by part of the x-ray beam being intercepted by the leading edge 52 of the outside diameter of tube 36. As long as the axis of tube 36 is misaligned with the central x-ray, the image defining circles 50 and 51 will be eccentric. The device is shifted in a sequence of steps until circles 50 and 51 become concentric as shown in FIG. 6 in which case it is known that the central x-ray is precisely perpendicular to the plane of image receptor 18. If, when perpendicularity is known, the central ray does not coincide with the center of the receptor, measures are taken to establish the center of the receptor on the same vertical line as the central ray and focal spot.

In systems that use radiographic film instead of an image intensifier, the test procedure can be carried out using a fluorescent sheet as the image receptor plane in which case the circular shadow patterns 50 and 51 may be visualized and the tube 36 repositioned until concentricity is obtained. If, in this case, as in the preceding case, the aperture provided by the tube bore is grossly misaligned, there will be no image of the inside diameter of the aperture but, instead, a foreshortened image of the length of the tube 36.

Although use of the new alignment device has been described in reference to a rather conventional x-ray table which has the x-ray tube mounted inside of the table body, it should be appreciated that the device may be used to align the central x-ray beam and image receptor in diagnostic systems where the x-ray source is not even mounted in a table such as when the source and image receptor are mounted on a C-arm or U-arm or other support.

I claim:

1. A device for determining when a selected ray in an x-ray beam which diverges from a focal spot is perpendicular to a predetermined plane, comprising:

a straight x-ray impermeable tube comprised of a wall having a concentric bore and having a length which is substantially greater than its inside and outside diameters, support means for said tube constructed and arranged to permit radiation from said focal spot to be projected generally axially of said tube along the inside and outside thereof and to permit said tube to be moved in the path of said beam, whereby perpendicularity of said selected ray will be indicated when the image of the inside and outside of said tube are concentric.

2. The device as in claim 1 wherein said support means comprises a block of x-ray permeable material having a substantially planar bottom surface, said tube being perpendicular to said surface.

3. The device as in claim 2 including a plurality of leveling screws threadingly engaged with said block and projecting from said surface, and a level device mounted on said support for indicating when a plane to which said tube is perpendicular is level.

4. A device for determining when a selected ray in an x-ray beam which diverges from a focal spot is perpendicular to a predetermined plane, including:
   a support comprising an x-ray permeable body,
   an x-ray impermeable tube disposed in said body,
   a level indicating device mounted on said body in such manner that when level is indicated the axis of said tube will be perpendicular to a level plane, and
   a plurality of leveling screws threadingly engaged with said support for establishing the level of said plane.

5. A device as in claim 4 wherein said support comprises a block of plastic material.

6. A device as in claim 5 wherein said plastic material is methyl methacrylate.

7. A device as in claim 4 wherein said tube is composed of stainless steel.

8. A method of determining when a selected ray in an x-ray beam emanating from a focal spot is directed onto a predetermined point of an image receptor plane, comprising the steps of:
   disposing an elongated x-ray impermeable circular tube in the intended path of said beam with the axis of said tube in substantial perpendicularity to said plane,
   turning on said x-ray beam and observing whether or not the shadow image of the wall of said tube on said receptor plane is concentric with the image produced by the bore of said tube, and if the images are not concentric, and
   shifting said tube and repeating said observation with the beams on until concentricity of the images is obtained at which time said ray will be perpendicular to said plane.

* * * * *